United States Patent
Hamada et al.

(10) Patent No.: US 11,458,079 B2
(45) Date of Patent: Oct. 4, 2022

(54) SUNSCREEN COSMETIC

(71) Applicants: JO COSMETICS CO., LTD., Tokyo (JP); MEISTERBIO CO., LTD., Okayama (JP)

(72) Inventors: Hiroki Hamada, Okayama (JP); Ryuta Yuasa, Tokyo (JP); Yui Matsuhashi, Tokyo (JP); Daisuke Uesugi, Tokyo (JP)

(73) Assignees: JO COSMETICS CO., LTD., Tokyo (JP); MEISTERBIO CO., LTD., Okayama (JP)

( * ) Notice: Subject to any disclaimer, the term of this patent is extended or adjusted under 35 U.S.C. 154(b) by 0 days.

(21) Appl. No.: 17/442,822

(22) PCT Filed: Feb. 28, 2020

(86) PCT No.: PCT/JP2020/008437
§ 371 (c)(1),
(2) Date: Sep. 24, 2021

(87) PCT Pub. No.: WO2020/195549
PCT Pub. Date: Oct. 1, 2020

(65) Prior Publication Data
US 2022/0087912 A1    Mar. 24, 2022

(30) Foreign Application Priority Data
Mar. 25, 2019    (JP) .............................. JP2019-056850

(51) Int. Cl.
| | |
|---|---|
| *A61K 8/29* | (2006.01) |
| *A61K 8/06* | (2006.01) |
| *A61K 8/27* | (2006.01) |
| *A61K 8/73* | (2006.01) |
| *A61Q 17/04* | (2006.01) |
| *A61K 8/19* | (2006.01) |
| *A61K 8/28* | (2006.01) |

(52) U.S. Cl.
CPC .................. *A61K 8/29* (2013.01); *A61K 8/06* (2013.01); *A61K 8/19* (2013.01); *A61K 8/27* (2013.01); *A61K 8/28* (2013.01); *A61K 8/73* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 2003/0180232 A1* | 9/2003 | Ishii | .......................... A61K 8/35 424/59 |
| 2008/0044365 A1 | 2/2008 | Simonnet et al. | |
| 2015/0098987 A1 | 4/2015 | Hamada et al. | |
| 2015/0152130 A1 | 6/2015 | Hamada et al. | |
| 2015/0359715 A1 | 12/2015 | Chevalier et al. | |
| 2018/0066005 A1 | 3/2018 | Hamada et al. | |

FOREIGN PATENT DOCUMENTS

| | | |
|---|---|---|
| JP | 2004-532790 A | 10/2004 |
| JP | 2008-001705 A | 1/2008 |
| JP | 2016-028018 A | 2/2016 |
| JP | 2016-503788 A | 2/2016 |
| WO | 2001/091695 A2 | 12/2001 |
| WO | 2010/072754 A1 | 7/2010 |

OTHER PUBLICATIONS

International Search Report dated Apr. 28, 2020 for International Application No. PCT/JP2020/008437, 4 pages with English translation.

Office Action dated Dec. 29, 2021 for corresponding Chinese Application No. 202080024387.8, 13 pages with English translation.

\* cited by examiner

*Primary Examiner* — Jennifer A Berrios
(74) *Attorney, Agent, or Firm* — MH2 Technology Law Group, LLP

(57) ABSTRACT

An object of the present invention is to provide a cosmetic composition for use in sunscreen that exhibits a sufficient effect with a reduced content of a UV protection agent, and to provide a cosmetic composition for use in sunscreen that has excellent texture, usability, and antioxidant action, while having a UV protection effect. In order to achieve this object, an emulsified cosmetic composition for use in sunscreen comprising (A) trans-resveratrol polysaccharide and (B) a UV protection agent is provided.

10 Claims, No Drawings

SUNSCREEN COSMETIC

CROSS-REFERENCE TO RELATED APPLICATIONS

This application is a U.S. National Stage application of PCT/JP2020/008437, filed 28 Feb. 2020, which claims priority to Japanese Application No. 2019-056850, filed 25 Mar. 2019, the entire disclosures of which are incorporated herein by reference in their entireties.

TECHNICAL FIELD

The present invention relates to an emulsified cosmetic composition for use in sunscreen comprising trans-resveratrol polysaccharide and a UV protection agent.

BACKGROUND ART

Conventionally, inorganic UV scattering agents, such as titanium dioxide, zinc oxide, or cerium oxide, or organic UV absorbing agents have been mixed into cosmetic compositions for the purpose of imparting a high UV protection function thereto. However, when a large amount of such a UV scattering agent or a UV absorbing agent is mixed into cosmetics for use in sunscreen, there are concerns, for example, that such cosmetics are poorly spread when applied to the skin, that the skin feels sticky, and that the skin is irritated. Therefore, efforts have been made to obtain cosmetic compositions for use in sunscreen that exhibit a higher UV protection effect with a lower amount of UV protection agent.

PTL 1 discloses an attempt to increase the sun protection factor (SPF value) by using concave particles of silicone material in an aqueous medium containing an organic and/or inorganic UV protection agent. Resveratrol is widely known to exhibit antioxidant action, such as protection from cell death induced by hydrogen peroxide or the like. PTL 2 discloses the use of resveratrol (which is referred to as resveratrol in this literature) and a derivative thereof as active ingredients of sunscreens. PTL 3 discloses trans-resveratrol polysaccharide and a cosmetic composition comprising the same.

CITATION LIST

Patent Literature

PTL 1: JP2008-001705A
PTL 2: JP2004-532790A
PTL 3: JP2016-028018A

SUMMARY OF INVENTION

Technical Problem

In the invention disclosed in PTL 1 relating to a cosmetic composition for use in sunscreen, a special powder component is added to synergistically increase the sunscreen effect. This causes a problem that the ease of spreading is reduced when this composition is applied to the skin.

The resveratrol disclosed in PTL 2 as an active ingredient of a sunscreen cosmetic composition is an oil-soluble component. Thus, the use thereof in the sunscreen cosmetic composition causes stickiness problems. Further, PTL 2 refers to a glycosylated derivative of resveratrol as a resveratrol derivative that can be contained in the sunscreen cosmetic composition. However, as described later in the Examples of the present specification, for example, the water solubility of resveratrol monosaccharide glycosides, such as piceid, is insufficient, and mass production of cosmetic compositions containing them is impractical.

Formulation Example 6 of PTL 3 discloses an emulsion foundation containing resveratrol polysaccharide and titanium dioxide. However, titanium dioxide generally contained as an essential ingredient in foundations is pigment-grade titanium oxide having a primary particle size of 0.2 to 0.3 μm used to give a white color, and is different from fine particle titanium oxide having a primary particle size of 5 nm to 100 nm used as a UV protection component. In addition, as described later, the UV protection effects of both components when combined with resveratrol polysaccharide are quite different.

An object of the present invention is to provide a cosmetic composition for use in sunscreen that exhibits a sufficient effect with a reduced content of a UV protection agent, which has somewhat negative effects on the human body. Another object of the present invention is to provide a cosmetic composition for use in sunscreen that has excellent texture (not sticky) or usability (easy to spread), or that does not cause white cast, while having the UV protection effect described above.

Solution to Problem

As a result of extensive studies to solve the above problems, the present inventors found that the UV protection effect of an emulsified cosmetic composition combining trans-resveratrol polysaccharide and a UV protection agent as active ingredients is synergistically improved compared to the effects of the respective active ingredients. The present inventors also found that this emulsified cosmetic composition has excellent texture and/or usability, or does not cause white cast.

The present invention has been completed based on these findings, and includes a wide range of inventions shown in the following embodiments.

Item 1. An emulsified cosmetic composition for use in sunscreen, comprising the following components (A) and (B):
(A) trans-resveratrol polysaccharide; and
(B) a UV protection agent.

Item 2. The emulsified cosmetic composition according to Item 1, wherein the trans-resveratrol polysaccharide is a compound in which a plurality of sugars are O-glycosidically linked to a hydroxyl group of trans-resveratrol.

Item 3. The emulsified cosmetic composition according to Item 2, wherein the O-glycosidic linkage is a linkage between a sugar and a hydroxyl group at position 3 and/or 4' of trans-resveratrol.

Item 4. The emulsified cosmetic composition according to Item 2 or 3, wherein the O-glycosidic linkage is a β-O-glycosidic linkage.

Item 5. The emulsified cosmetic composition according to any one of Items 2 to 4, wherein the sugar is at least one monosaccharide selected from the group consisting of aldose, ketose, and deoxysugar, all of which can have any of an oxylose ring, oxetose ring, pyranose ring, furanose ring, septanose ring, or octanose ring structure; or a polysaccharide in which two or more of these monosaccharides are O-glycosidically linked to each other.

Item 6. The emulsified cosmetic composition according to Item 5, wherein the monosaccharide is any one selected from the group consisting of glucose, maltose, and galactose.

Item 7. The emulsified cosmetic composition according to Item 5, wherein the polysaccharide is a polysaccharide in which two or more monosaccharides selected from the group consisting of glucose, maltose, and galactose are O-glycosidically linked to each other.

Item 8. The emulsified cosmetic composition according to Item 6 or 7, wherein the polysaccharide is a polysaccharide in which two or more monosaccharides are (1-1) glycosidically linked, (1-2) glycosidically linked, (1-3) glycosidically linked, (1-4) glycosidically linked, or (1-6) glycosidically linked to each other.

Item 9. The emulsified cosmetic composition according to any one of Items 6 to 8, wherein the polysaccharide is a polysaccharide in which two or more monosaccharides are α-glycosidically linked or β-glycosidically linked.

Item 10. The emulsified cosmetic composition according to any one of Items 1 to 9, wherein the trans-resveratrol polysaccharide is at least one compound selected from the group consisting of:

trans-resveratrol 3-O-β-D-diglucoside, or a compound in which a plurality of sugars are further glycosidically linked to the hydroxyl group at position 1 of its sugar residue;

trans-resveratrol 4'-O-β-D-diglucoside, or a compound in which a plurality of sugars are further glycosidically linked to the hydroxyl group at position 1 of its sugar residue; and trans-resveratrol-O-β-D-3 monoglucoside 4' monoglucoside, or a compound in which a plurality of sugars are further glycosidically linked to the hydroxyl group at position 1 of the sugar residue linked to position 3 thereof, the hydroxyl group at position 1 of the sugar residue linked to position 4' thereof, or the hydroxyl groups at both positions.

Item 11. The emulsified cosmetic composition according to any one of Items 1 to 10, wherein the trans-resveratrol polysaccharide is any of compounds represented by the following formulas (1) to (3):

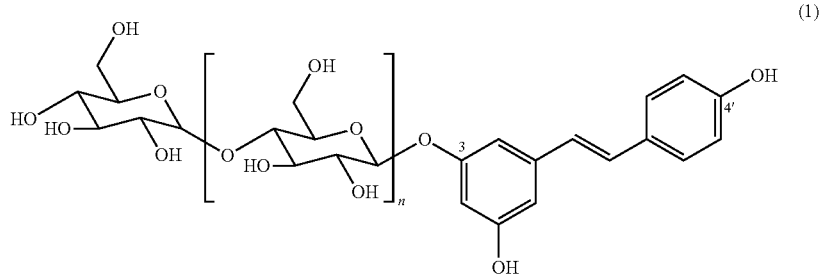

(1)

wherein n is an integer of 1 to 15,
all (1-4) glycosidic linkages in the formula are α-linkages, and
an O-glycosidic linkage at position 3 of resveratrol in the formula is a β-linkage;

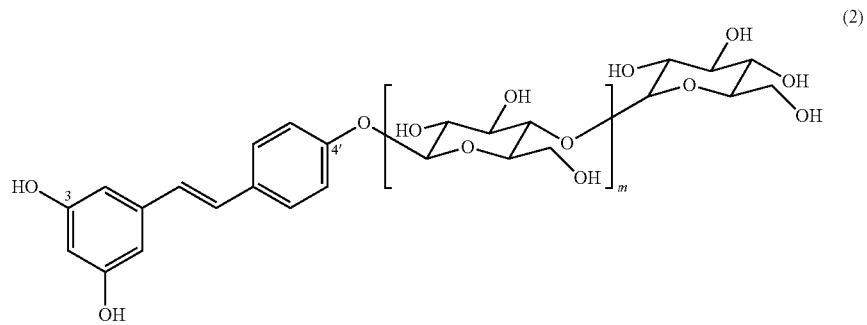

(2)

wherein m is an integer of 1 to 15,
all (1-4) glycosidic linkages in the formula are α-linkages, and
an O-glycosidic linkage at position 4' of resveratrol in the formula is a β-linkage; or

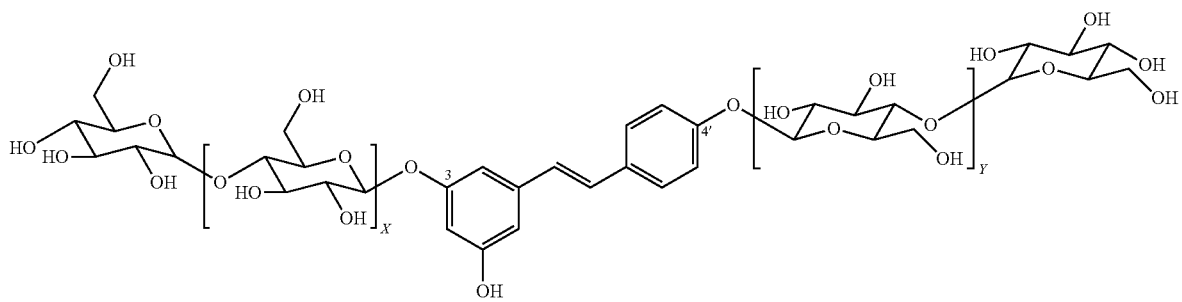

(3)

wherein X and Y are both an integer of 0 or more, and the sum of X and Y is 15 or less,
all (1-4) glycosidic linkages in the formula are α-linkages, and O-glycosidic linkages at positions 3 and 4' of resveratrol in the formula are β-linkages.

Item 12. The emulsified cosmetic composition according to any one of Items 1 to 11, wherein the UV protection agent is a UV scattering agent and/or a UV absorbing agent.

Item 13. The emulsified cosmetic composition according to Item 12, wherein the UV scattering agent is at least one member selected from the group consisting of fine particle titanium oxide, fine particle zinc oxide, fine particle iron oxide, fine particle cerium oxide, and fine particle zirconium oxide.

Item 14. The emulsified cosmetic composition according to Item 12 or 13, wherein the UV scattering agent has a number average particle size of 5 nm or more and 100 nm or less.

Item 15. The emulsified cosmetic composition according to any one of Items 12 to 14, wherein the UV scattering agent has a hydrophobized surface.

Item 16. The emulsified cosmetic composition according to Item 15, wherein the hydrophobization treatment is hydrophobization treatment using silicone, a metal soap, an N-acyl amino acid salt, or a perfluoroalkyl compound.

Item 17. The emulsified cosmetic composition according to Item 12, wherein the UV absorbing agent is at least one member selected from the group consisting of a benzoic acid UV absorbing agent, an anthranilic acid UV absorbing agent, a salicylic acid UV absorbing agent, a cinnamic acid UV absorbing agent, a benzophenone UV absorbing agent, a triazine UV absorbing agent, 3-(4'-methylbenzylidene)-dl-camphor, 3-benzylidene-dl-camphor, urocanic acid ethyl ester, 2-phenyl-5-methylbenzoxazole, 2,2'-hydroxy-5-methylphenylbenzotriazole, 2-(2'-hydroxy-5-t-octylphenyl)benzotriazole, dibenzalazine, dianisoylmethane, 4-methoxy-4'-t-butyldibenzoylmethane, 5-(3,3-dimethyl-2-norbonylidene)-3-pentan-2-one, and octocrylene.

Item 18. The emulsified cosmetic composition according to Item 17, wherein the benzoic acid UV absorbing agent is at least one member selected from the group consisting of para-aminobenzoic acid, glyceryl para-aminobenzoate, ethyl dihydroxypropyl para-aminobenzoate, N-ethoxylate para-aminobenzoic acid ethyl ester, N-dimethyl para-aminobenzoic acid ethyl ester, N-dimethyl para-aminobenzoic acid butyl ester, N-dimethyl para-aminobenzoic acid amyl ester, octyl dimethyl para-aminobenzoate, and hexyl diethylaminohydroxybenzoyl benzoate.

Item 19. The emulsified cosmetic composition according to Item 17, wherein the anthranilic acid UV absorbing agent is homomenthyl-N-acetylanthranilate.

Item 20. The emulsified cosmetic composition according to Item 17, wherein the salicylic acid UV absorbing agent is at least one member selected from the group consisting of amyl salicylate, menthyl salicylate, homomenthyl salicylate, octyl salicylate, phenyl salicylate, benzyl salicylate, and p-isopropanol phenyl salicylate.

Item 21. The emulsified cosmetic composition according to Item 17, wherein the cinnamic acid UV absorbing agent is at least one member selected from the group consisting of octyl cinnamate, ethyl-4-isopropylcinnamate, ethyl-2,4-diisopropylcinnamate, methyl-2,4-diisopropylcinnamate, propyl-p-methoxycinnamate, isopropyl-p-methoxycinnamate, isoamyl-p-methoxycinnamate, ethylhexyl methoxycinnamate, 2-ethoxyethyl-p-methoxycinnamate, cyclohexyl-p-methoxycinnamate, ethyl-α-cyano-β-phenylcinnamate, 2-ethylhexyl-α-cyano-β-phenylcinnamate, and glyceryl mono-2-ethylhexanoyl diparamethoxycinnamate.

Item 22. The emulsified cosmetic composition according to Item 17, wherein the benzophenone UV absorbing agent is at least one member selected from the group consisting of 2,4-dihydroxybenzophenone, 2,2'-dihydroxy-4-methoxybenzophenone, 2,2'-dihydroxy-4,4'-dihydroxybenzophenone, 2-hydroxy-4-methoxybenzophenone, 2-hydroxy-4-methoxy-4'-methylbenzophenone, 2-hydroxy-4-methoxybenzophenone, 4-phenylbenzophenone, 2-ethylhexyl-4'-phenylbenzophenone-2-carboxylate, 2-hydroxy-4-n-octoxybenzophenone, and 4-hydroxy-3-carboxybenzophenone.

Item 23. The emulsified cosmetic composition according to Item 17, wherein the triazine UV absorbing agent is at least one member selected from the group consisting of 2,4,6-tris[4-(2-ethylhexyloxycarbonyl)anilino]-1,3,5-triazine and 2,4-bis-[{4-(2-ethylhexyloxy)-2-hydroxy}-phenyl]-6-(4-methoxyphenyl)-1,3,5-triazine.

Item 24. The emulsified cosmetic composition according to any one of Items 1 to 23, wherein the type of emulsion is any one of oil-in-water, water-in-oil, water-in-oil-in-water, or oil-in-water-in-oil.

Item 25. The emulsified cosmetic composition according to any one of Items 1 to 24, wherein the trans-resveratrol polysaccharide is present in an aqueous phase, and the UV protection agent is present in an oil phase.

Advantageous Effects of Invention

Due to the combined use of component (A) (trans-resveratrol polysaccharide) and component (B) (UV protection agent), the emulsified cosmetic composition for use in sunscreen of the present invention has a synergistically higher UV protection effect than emulsified cosmetic compositions obtained by mixing each of the above components alone. Further, in the emulsified cosmetic for use in sunscreen of the present invention, which is composed of an aqueous phase and an oil phase, trans-resveratrol polysaccharide (A) can be dissolved in the aqueous phase, and a UV protection agent as component (B) can be dissolved or dispersed in the oil phase. Accordingly, for example, compared with the case of mixing a large amount of UV protection agent in the oil phase, the amount of the oil phase can be reduced, the viscosity of the oil phase can be kept low, and there is no decrease in texture, such as oiliness and stickiness, or there is no decrease in usability, such as ease of spreading on the skin.

DESCRIPTION OF EMBODIMENTS

Component (A): Trans-Resveratrol Polysaccharide

Component (A) (trans-resveratrol polysaccharide) contained in the emulsified cosmetic composition for use in sunscreen of the present invention has higher water solubility due to the linkage of a plurality of sugars to oil-soluble trans-resveratrol, and thus can be stably mixed into the aqueous phase of the emulsified cosmetic composition. Therefore, emulsified cosmetic compositions containing trans-resveratrol polysaccharide are less sticky and can give a refreshing texture, compared with those containing an oil-soluble UV absorbing agent. Further, compared with those containing fine particle inorganic powder, emulsified cosmetic compositions that are easily spread (excellent usability) or that do not cause white cast (good appearance) can be obtained.

The trans-resveratrol polysaccharide is also called trans-resveratrol polysaccharide glycoside, which is a compound in which a plurality of sugars are linked to trans-resveratrol. Trans-resveratrol is a stilbene compound (also referred to as "stilbenoid") having hydroxyl groups at positions 3, 4', and 5 thereof. The trans-resveratrol polysaccharide may be a compound in which a polysaccharide composed of two or more monosaccharides is glycosidically linked to one substituent of trans-resveratrol, or a compound in which a monosaccharide and/or a polysaccharide composed of two or more monosaccharides is glycosidically linked to two or more different substituents of trans-resveratrol.

The specific number of sugars linked to trans-resveratrol is not particularly limited within the range in which the effects of the present invention are exhibited. Specifically, the number of sugars is, for example, about 2, 3, 4, 5, 6, 7, 8, 9, 10, 11, 12, 13, 14, 15, 16, or 17. In view of the ease of production of trans-resveratrol polysaccharide, described later, the number of sugars is preferably 2, 3, 4, 5, 6, 7, 8, 9, 10, 11, 12, 13, 14, or 15; and more preferably about 2, 3, 4, 5, 6, 7, 8, 9, or 10.

The resveratrol polysaccharide glycoside may be a mixture of different compounds in which various numbers of sugars are glycosidically linked to trans-resveratrol. It is preferable that such a mixture contains as little as possible resveratrol aglycone and resveratrol monosaccharide glycoside (e.g., piceid), in view of the effect of efficiently dissolving this mixture in the aqueous phase in the production process of the emulsified cosmetic composition for use in sunscreen of the present invention. The total content of resveratrol aglycone and resveratrol monosaccharide glycoside in the mixture is not particularly limited within the range in which the above effect of the invention can be obtained. Specifically, the total content of resveratrol aglycone and resveratrol monosaccharide glycoside based on 100 mass % of the mixture can be less than 50 mass %, preferably less than 40 mass %, more preferably less than 30 mass %, and most preferably less than 27 mass %.

The mode of the glycosidic linkage between trans-resveratrol and sugar in the trans-resveratrol polysaccharide is not particularly limited within the range in which the effects of the present invention are exhibited. Specific examples include an O-glycosidic linkage, a C-glycosidic linkage, an N-glycosidic linkage, an S-glycosidic linkage, and the like. In view of the ease of obtaining the above sugars or the ease of glycosylation of trans-resveratrol, an O-glycosidic linkage is preferable.

The site of trans-resveratrol to which sugar is glycosidically linked in the trans-resveratrol polysaccharide is not particularly limited within the range in which the effects of the present invention are exhibited. For example, when sugar is O-glycosidically linked to trans-resveratrol, examples of the linkage site include the hydroxyl group at position 3, 4', or 5 of trans-resveratrol. Further, examples of the linkage site other than the O-glycosidic linkage include any of the carbon atoms of trans-resveratrol. In view of the ease of production of trans-resveratrol polysaccharide or the ease of obtaining the above sugars, it is preferable that sugar is O-glycosidically linked to one or more hydroxyl groups at any position 3, 4', or 5 of trans-resveratrol. Further, in view of the efficient functioning of the trans-resveratrol polysaccharide, it is more preferable that sugar is O-glycosidically linked to position 3 and/or 4' of trans-resveratrol.

The mode of the anomeric linkage of sugar to trans-resveratrol in the trans-resveratrol polysaccharide is not particularly limited within the range in which the effects of the present invention are exhibited. Specifically, the anomeric linkage can be an α-linkage or a β-linkage. In view of the structural stability of the trans-resveratrol polysaccharide when applied to the skin, a β-linkage is preferable.

The sugars glycosidically linked to trans-resveratrol in the trans-resveratrol polysaccharide are not particularly limited within the range in which the effects of the present invention are exhibited. Specifically, the sugars can be monosaccharides or polysaccharides.

The monosaccharides mentioned above are not particularly limited within the range in which the effects of the present invention are exhibited. Specific examples include any monosaccharide of aldose, ketose, or deoxysugar, all of which can have any of an oxylose ring, oxetose ring, pyranose ring, furanose ring, septanose ring, or octanose ring structure. Among these monosaccharides, in view of the ease of production of trans-resveratrol polysaccharide or the availability of these monosaccharides at low cost, glucose, maltose, or galactose is preferred, and glucose is most preferred. The above monosaccharides can also be oxidized (e.g. uronic acid, aldonic acid, or aldaric acid) or reduced (e.g. alditol).

The polysaccharides mentioned above are sugars in which two or more monosaccharides are glycosidically linked, and are not particularly limited within the range in which the effects of the present invention are exhibited. Specific examples include polysaccharides in which two or more monosaccharides of aldose, ketose, and deoxysugar, all of which can have any of an oxylose ring, oxetose ring, pyranose ring, furanose ring, septanose ring, or octanose ring structure, are glycosidically linked. Such monosaccharides can be the same as those described in detail above as the sugars to be glycosidically linked to trans-resveratrol.

The mode of the glycosidic linkage between two or more monosaccharides in the polysaccharide is a linkage mode formed between the anomeric carbon of one monosaccharide to be linked and the hydroxyl group of the other monosaccharide, and is not particularly limited within the range in which the effects of the present invention are exhibited. Specifically, two or more monosaccharides are linked to each other through a (1-1) glycosidic linkage, a (1-2) glycosidic linkage, a (1-3) glycosidic linkage, a (1-4) glycosidic linkage, or a (1-6) glycosidic linkage. In view of the ease of production of the trans-resveratrol polysaccharide, it is preferable that the glycosidic linkages among all the monosaccharides constituting the polysaccharide are the same. Further, in view of the ease of production of the trans-resveratrol polysaccharide, it is preferable that the glycosidic linkages among all the monosaccharides constituting the specific polysaccharide are (1-4) glycosidic linkages, (1-3) glycosidic linkages, or (1-6) glycosidic linkages, and most preferably (1-4) glycosidic linkages.

The mode of the anomeric linkage between two or more monosaccharides in the polysaccharide is not particularly limited within the range in which the effects of the present invention are exhibited. Specifically, the anomeric linkage may be an α-linkage or a β-linkage. In view of the ease of production of the trans-resveratrol polysaccharide, it is preferable that the anomeric linkages among all the monosaccharides constituting the polysaccharide are the same. Further, in view of the ease of conformity of the emulsified cosmetic composition containing trans-resveratrol polysaccharide to the skin, it is preferable that the anomeric linkages among all the monosaccharides constituting the polysaccharide are α-linkages.

The trans-resveratrol polysaccharide is not particularly limited within the range in which the effects of the present invention are exhibited. Specific examples include trans-resveratrol 3-O-β-D-diglucoside, or a compound in which a plurality of sugars are further glycosidically linked to the hydroxyl group at position 1 of its sugar residue; trans-resveratrol 4'-O-β-D-diglucoside, or a compound in which a plurality of sugars are further glycosidically linked to the hydroxyl group at position 1 of its sugar residue; and trans-resveratrol-O-β-D-3 monoglucoside 4' monoglucoside, or a compound in which a plurality of sugars are further glycosidically linked to the hydroxyl group at position 1 of the sugar residue linked to position 4' thereof, the hydroxyl group at position 1 of the sugar residue linked to position 3 thereof, or the hydroxyl groups at both positions. These compounds can be used singly or in combination of two or more as the trans-resveratrol polysaccharide. The plurality of sugars to be further glycosidically linked can be the same as the monosaccharides and/or polysaccharides described in detail above.

Among the trans-resveratrol polysaccharides described above, a compound represented by any of the following formulas (1) to (3) is preferred.

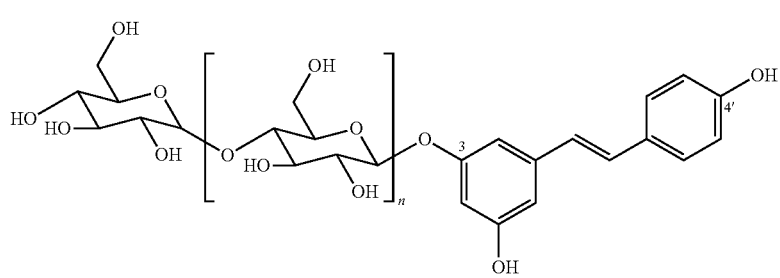

(1)

wherein n is an integer of 1 to 15,
all (1-4) glycosidic linkages in the formula are α-linkages, and
an O-glycosidic linkage at position 3 of resveratrol in the formula is a β-linkage.

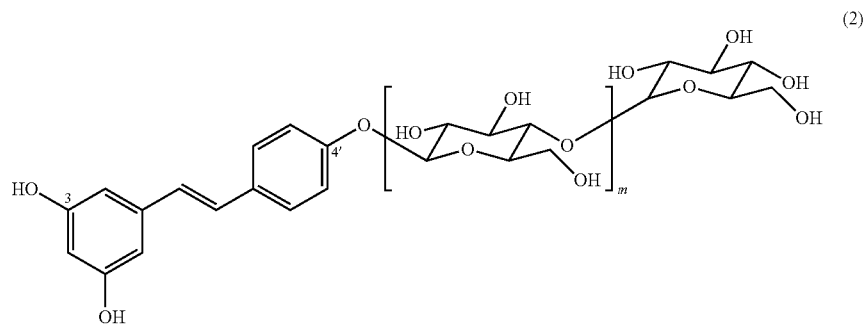

(2)

wherein m is an integer of 1 to 15,
all (1-4) glycosidic linkages in the formula are α-linkages, and
an O-glycosidic linkage at position 4' of resveratrol in the formula is a β-linkage.

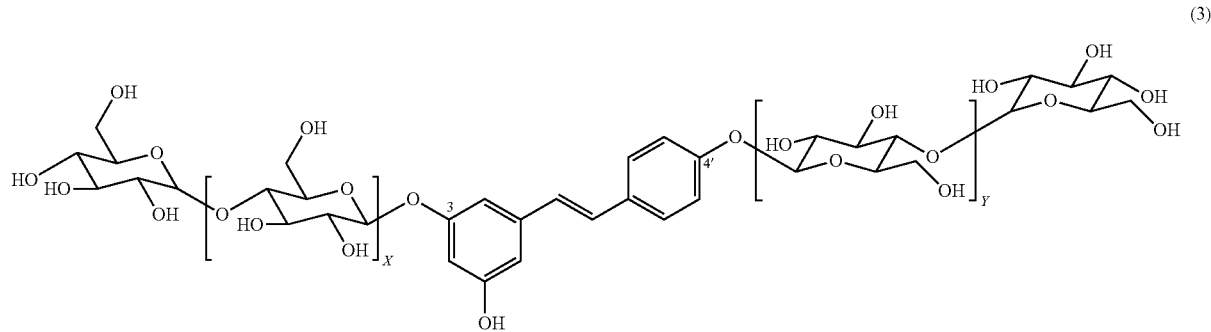

(3)

wherein X and Y are both an integer of 0 or more, and the sum of X and Y is 15 or less,
all (1-4) glycosidic linkages in the formula are α-linkages, and O-glycosidic linkages at positions 3 and 4' of resveratrol in the formula are β-linkages.

The trans-resveratrol polysaccharides can be purchased from the market, or can be produced by known methods. For example, the trans-resveratrol polysaccharide can be easily produced by using the method disclosed in JP6467762B in such a manner that trans-resveratrol is glycosylated, and, for example, cyclodextrin glucanotransferase, such as Contizyme (Amano Enzyme Inc.), and commercially available cyclodextrin are used for the obtained trans-resveratrol monosaccharide glycoside.

The content ratio of component (A) (trans-resveratrol polysaccharide) in the emulsified cosmetic composition for use in sunscreen of the present invention is not particularly limited within the range in which the effects of the present invention are exhibited. Specifically, the content of trans-resveratrol polysaccharide based on 100 mass % of the emulsified cosmetic composition for use in sunscreen is generally set to preferably about 0.0001 to 30 mass %, more preferably about 0.1 to 25 mass %, and even more preferably about 1 to 20 mass %. If the content of trans-resveratrol polysaccharide is overly low, a high sunscreen effect cannot be obtained, and a synergistic effect due to the combined use with a UV protection agent cannot be sufficiently obtained. In contrast, if the content of trans-resveratrol polysaccharide is overly large, the efficiency of the sunscreen effect with respect to the mixing amount is reduced, which is not economical.

(B) UV Protection Agent

Component (B) (UV protection agent) contained in the emulsified cosmetic composition for use in sunscreen of the present invention is not particularly limited as long as it is an agent that can be contained in the emulsified cosmetic composition and that exhibits a UV protection effect. Specifically, a UV scattering agent or a UV absorbing agent can be used.

The UV scattering agent is not particularly limited within the range in which the effects of the present invention are exhibited. Examples include fine particle inorganic substances. Specific examples include fine particle titanium oxide, fine particle zinc oxide, fine particle iron oxide, fine particle cerium oxide, fine particle zirconium oxide, and the like. These UV scattering agents can be contained singly or in combination of two or more in the emulsified cosmetic composition for use in sunscreen of the present invention. The shape of these fine particles is not particularly limited within the range in which the effects of the present invention are exhibited. Specific examples include an amorphous, granular, spherical, needle-like, spindle-like, or plate-like shape.

The UV scattering agent is preferably one that has a hydrophobized surface, from the viewpoint of the water resistance and sustainability of the emulsified cosmetic composition for use in sunscreen of the present invention. The surface hydrophobization treatment is not particularly limited within the range in which the effects of the present invention are exhibited. Specific examples include silicone, metal soaps, N-acyl amino acid salts, perfluoroalkyl compounds, and the like. These hydrophobization treatments can be used singly or in combination of two or more for the surface treatment of the UV scattering agent.

The number average particle size of the UV scattering agent is not particularly limited within the range in which the effects of the present invention are exhibited. Specific examples include fine particles with a number average particle size of 5 nm or more and 100 nm or less, which are known to exhibit a UV scattering effect. Preferred are fine particles with a number average particle size of 8 nm or more and 85 nm or less, and more preferred are fine particles with a number average particle size of 10 nm or more and 35 nm or less. If the number average particle size is overly small, the UV protection effect is reduced. If the number average particle size is overly large, the UV protection effect is reduced, and the transparency is also reduced. In the present invention, the primary particle size refers to the length of the shortest part of the particle passing through the center, when the particle is not spherical. For the number average particle size of the UV scattering agent used in the Examples described later, values from the material manufacturer's catalogue etc. are given where available.

The UV absorbing agent is not particularly limited within the range in which the effects of the present invention are exhibited. For example, oil-soluble UV absorbing agents are preferred. Specific examples include benzoic acid UV absorbing agents, anthranilic acid UV absorbing agents, salicylic acid UV absorbing agents, cinnamic acid UV absorbing agents, benzophenone UV absorbing agents, triazine UV absorbing agents, and the like. These UV absorbing agents can be contained singly or in combination of two or more in the emulsified cosmetic composition for use in sunscreen of the present invention.

The benzoic acid UV absorbing agents mentioned above are not particularly limited within the range in which the effects of the present invention are exhibited. Specific examples include para-aminobenzoic acid (hereinafter also abbreviated as "PABA"), glyceryl PABA, ethyl dihydroxypropyl PABA, N-ethoxylate PABA ethyl ester, N-dimethyl PABA ethyl ester, N-dimethyl PABA butyl ester, N-dimethyl PABA amyl ester, octyl dimethyl PABA, diethylaminohydroxybenzoyl hexyl benzoate, and the like. These benzoic acid UV absorbing agents can be contained singly or in combination of two or more in the emulsified cosmetic composition for use in sunscreen of the present invention.

The anthranilic acid UV absorbing agents mentioned above are not particularly limited within the range in which the effects of the present invention are exhibited. Specific examples include homomenthyl-N-acetylanthranilate and the like.

The salicylic acid UV absorbing agents mentioned above are not particularly limited within the range in which the effects of the present invention are exhibited. Specific examples include amyl salicylate, menthyl salicylate, homomenthyl salicylate, octyl salicylate, phenyl salicylate, benzyl salicylate, p-isopropanol phenyl salicylate, and the like. These salicylic acid UV absorbing agents can be contained singly or in combination of two or more in the emulsified cosmetic composition for use in sunscreen of the present invention.

The cinnamic acid UV absorbing agents mentioned above are not particularly limited within the range in which the effects of the present invention are exhibited. Specific examples include octyl cinnamate, ethyl-4-isopropylcinnamate, ethyl-2,4-diisopropylcinnamate, methyl-2,4-diisopropylcinnamate, propyl-p-methoxycinnamate, isopropyl-p-methoxycinnamate, isoamyl-p-methoxycinnamate, ethylhexyl methoxycinnamate, 2-ethoxyethyl-p-methoxycinnamate, cyclohexyl-p-methoxycinnamate, ethyl-α-cyano-β-phenylcinnamate, 2-ethylhexyl-α-cyano-β-phenylcinnamate, glyceryl mono-2-ethylhexanoyl diparamethoxycinnamate, and the like. These cinnamic acid UV absorbing agents can be contained singly or in combination of two or more in the emulsified cosmetic composition for use in sunscreen of the present invention.

The benzophenone UV absorbing agents mentioned above are not particularly limited within the range in which the effects of the present invention are exhibited. Specific examples include 2,4-dihydroxybenzophenone, 2,2'-dihydroxy-4-methoxybenzophenone, 2,2'-dihydroxy-4,4'-dihydroxybenzophenone, 2-hydroxy-4-methoxybenzophenone, 2-hydroxy-4-methoxy-4'-methylbenzophenone, 2-hydroxy-4-methoxybenzophenone, 4-phenylbenzophenone, 2-ethylhexyl-4'-phenylbenzophenone-2-carboxylate, 2-hydroxy-4-n-octoxybenzophenone, 4-hydroxy-3-carboxybenzophenone, and the like. These benzophenone UV absorbing agents can be contained singly or in combination of two or more in the emulsified cosmetic composition for use in sunscreen of the present invention.

The triazine UV absorbing agents mentioned above are not particularly limited within the range in which the effects of the present invention are exhibited. Specific examples include 2,4,6-tris[4-(2-ethylhexyloxycarbonyl)anilino]-1,3,5-triazine, 2,4-bis-[{4-(2-ethylhexyloxy)-2-hydroxy}-phenyl]-6-(4-methoxyphenyl)-1,3,5-triazine, and the like. These triazine UV absorbing agents can be contained singly or in combination of two or more in the emulsified cosmetic composition for use in sunscreen of the present invention.

In addition to the UV absorbing agents mentioned above, 3-(4'-methylbenzylidene)-dl-camphor, 3-benzylidene-dl-camphor, urocanic acid ethyl ester, 2-phenyl-5-methylbenzoxazole, 2,2'-hydroxy-5-methylphenylbenzotriazole, 2-(2'-hydroxy-5-t-octylphenyl)benzotriazole, dibenzalazine, dianisoylmethane, 4-methoxy-4'-t-butyldibenzoylmethane, 5-(3,3-dimethyl-2-norbonylidene)-3-pentan-2-one, octocrylene, and the like. These components can be contained singly or in combination of two or more in the emulsified cosmetic composition for use in sunscreen of the present invention.

Among the UV absorbing agents mentioned above, ethylhexyl methoxycinnamate or diethylaminohydroxybenzoyl hexyl benzoate is preferred, from the viewpoint of the UV protection effect to be exhibited or compatibility with a base that can be contained in the cosmetic composition.

The content of component (B) in the emulsified cosmetic composition for use in sunscreen of the present invention is not particularly limited within the range in which the effects of the present invention are exhibited. Specifically, the content of component (B) is preferably 0.5 to 50 mass %, more preferably 1 to 40 mass %, and even more preferably 2 to 30 mass %, based on 100 mass % of the emulsified cosmetic composition for use in sunscreen. Due to the content of component (B) within such a range, a high sunscreen effect can be obtained, and a synergistic effect due to the combined use with component (A) can also be sufficiently obtained. Further, due to the content of component (B) within such a range, the emulsified cosmetic composition for use in sunscreen of the present invention has the effect of being less sticky and not reducing the ease of spreading on the skin. Moreover, because the efficiency of the sunscreen effect with respect to the content of component (B) is higher, the emulsified cosmetic composition for use in sunscreen of the present invention also has the effect of being economical.

In addition to components (A) and (B) described above, the emulsified cosmetic composition for use in sunscreen of the present invention may contain other components generally used in cosmetic composition preparations. Such other components may be suitably selected within the range in which the effects of the present invention are exhibited, and are not particularly limited. Specific examples include water (purified water, hot spring water, deep water, etc.), oily agents, surfactants, metal soaps, gelling agents, powders, alcohols, water-soluble polymers, film-forming agents, resins, clathrate compounds, antimicrobial agents, fragrances, deodorants, salts, pH regulators, coolants, animal and/or microbial extracts, plant extracts, blood circulation promoters, astringents, antiseborrheic agents, active oxygen scavengers, cell stimulants, moisturizers, keratolytic agents, enzymes, hormones, vitamins, and the like. These other components can be contained singly or in combination of two or more in the emulsified cosmetic composition for use in sunscreen of the present invention.

As the oily agents mentioned above as other components that can be contained in the emulsified cosmetic composition for use in sunscreen of the present invention, any oily agents can be used regardless of whether they are natural oils or synthetic oils, the synthesis method thereof, and whether they are solid, semi-solid, or liquid, as long as they can be contained in the cosmetic composition. Such oily agents can be suitably selected within the range in which the effects of the present invention are exhibited, and are not particularly limited. Specific examples include hydrocarbons, waxes, fatty acids, higher alcohols, ester oils, silicone oils, fluorine-based oils, and the like. These oily agents can be contained singly or in combination of two or more in the emulsified cosmetic composition for use in sunscreen of the present invention.

Specific examples of the oily agents mentioned above include hydrocarbons, such as squalane, squalene, ceresin, paraffin, paraffin wax, liquid paraffin, pristane, polyisobutylene, microcrystalline wax, and petrolatum; waxes, such as beeswax, carnauba wax, candelilla wax, and whale wax; animal oils, such as beef tallow, neatsfoot oil, beef bone fat, hardened beef tallow, hardened oil, turtle oil, pork fat, horse fat, mink oil, liver oil, and egg yolk oil; lanolin and lanolin derivatives, such as liquid lanolin, reduced lanolin, lanolin alcohol, hard lanolin, lanolin acetate, lanolin fatty acid isopropyl, polyoxyethylene (hereinafter also abbreviated as "POE") lanolin alcohol ether, POE lanolin alcohol acetate, lanolin fatty acid polyethylene glycol, and POE hydrogenated lanolin alcohol ether; fatty acids, such as lauric acid, myristic acid, palmitic acid, stearic acid, behenic acid, undecylenic acid, oleic acid, arachidonic acid, docosahexaenoic acid (DHA), isostearic acid, and 12-hydroxystearic acid; higher alcohols, such as lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecanol, cholesterol, phytosterol, sitosterol, lanosterol, POE cholesterol ether, and monostearylglycerin ether (batyl alcohol); ester oils, such as diisobutyl adipate, 2-hexyldecyl adipate, di-2-heptylundecyl adipate, N-alkyl glycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearyl, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, N-lauroyl-L-glutamate-2-octyldodecyl ester, and diisostearyl malate; glyceride oils, such as acetoglyceride, glyceride triisooctanoate, glyceride triisostearate, glyceride triisopalmitate, glyceride tri-2-ethylhexanoate, glyceride monostearate, glyceride di-2-heptylundecanoate, and glyceride trimyristate; higher alkoxy-modified silicones, such as dimethylpolysiloxane, methylphenylpolysiloxane, methylhydrogenpolysiloxane, octamethylcyclotetrasiloxane, decamethylcyclopentasiloxane, dodecamethylcyclohexasiloxane, tetramethyltetrahydrogencyclotetrasiloxane, and stearoxy silicone; silicone-based oily agents, such as higher fatty acid-modified silicone, silicone resin, silicone rubber, and silicone oil; fluorine-based oily agents, such as perfluoropolyether, perfluorodecalin, and perfluorooctane; and the like. These oily agents can be contained singly or in combination of two or more in the emulsified cosmetic composition for use in sunscreen of the present invention.

The surfactants mentioned above as other components that can be contained in the emulsified cosmetic composition for use in sunscreen of the present invention are not particularly limited within the range in which the effects of the present invention are exhibited. Specifically, anionic, cationic, nonionic, or amphoteric surfactants can be used.

The anionic surfactants mentioned above are not particularly limited within the range in which the effects of the present invention are exhibited. Specific examples include fatty acid soaps, such as potassium isostearate, sodium stearate, and triethanolamine palmitate; carboxylic acid salts, such as alkyl ether carboxylic acids and salts thereof, and condensates of amino acids and fatty acids; alkylsulfonic acids, alkenesulfonic acid salts, and sulfonic acid salts of fatty acid esters; sulfonic acid salts of fatty acid amides, sulfonic acid salts of alkylsulfonic acid salts and formalin condensates thereof, alkylsulfuric acid ester salts, secondary higher alcohol sulfuric acid ester salts, alkyl or aryl ether sulfuric acid ester salts, sulfuric acid ester salts of fatty acid esters, sulfuric acid ester salts of fatty acid alkylolamides, sulfuric acid ester salts such as turkey red oil, alkyl phosphates, alkyl ether phosphates, alkyl aryl ether phosphates, amide phosphates, N-acyl amino acid-based surfactants; and the like. These anionic surfactants can be contained singly or in combination of two or more in the emulsified cosmetic composition for use in sunscreen of the present invention.

The cationic surfactants mentioned above are not particularly limited within the range in which the effects of the present invention are exhibited. Specific examples include amine salts, such as alkylamine salts, and polyamine or amino alcohol fatty acid derivatives; alkyl quaternary ammonium salts, aromatic quaternary ammonium salts, pyridinium salts or imidazolium salts; and the like. These cationic surfactants can be contained singly or in combination of two or more in the emulsified cosmetic composition for use in sunscreen of the present invention.

The nonionic surfactants mentioned above are not particularly limited within the range in which the effects of the present invention are exhibited. Specific examples include sorbitan fatty acid ester, glycerin fatty acid ester, polyglycerin fatty acid ester, propylene glycol fatty acid ester, polyethylene glycol fatty acid ester, sucrose fatty acid ester, polyoxyethylene alkyl ether, polyoxypropylene alkyl ether, polyoxyethylene alkyl phenyl ether, polyoxyethylene fatty acid ester, polyoxyethylene sorbitan fatty acid ester, polyoxyethylene sorbitol fatty acid ester, polyoxyethylene glycerin fatty acid ester, polyoxyethylene propylene glycol fatty acid ester, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, polyoxyalkylene-modified organopolysiloxane, polyoxyalkylene-alkyl co-modified organopolysiloxane, alkanolamide, sugar ether, sugar amide, and the like. These components can be contained singly or in combination of two or more in the emulsified cosmetic composition for use in sunscreen of the present invention.

The amphoteric surfactants mentioned above are not particularly limited within the range in which the effects of the present invention are exhibited. Specific examples include betaine, aminocarboxylates, imidazoline derivatives, and the like. These amphoteric surfactants can be contained singly or in combination of two or more in the emulsified cosmetic composition for use in sunscreen of the present invention.

The metal soaps mentioned above as other components that can be contained in the emulsified cosmetic composition for use in sunscreen of the present invention are not particularly limited within the range in which the effects of the present invention are exhibited. Specific examples include aluminum 12-hydroxystearate, zinc stearate, aluminum stearate, calcium stearate, magnesium stearate, zinc myristate, magnesium myristate, zinc cetyl phosphate, calcium cetyl phosphate, sodium zinc cetyl phosphate, zinc laurate, zinc undecylenate, and the like. These metal soaps can be contained singly or in combination of two or more in the emulsified cosmetic composition for use in sunscreen of the present invention.

The gelling agents mentioned above as other components that can be contained in the emulsified cosmetic composition for use in sunscreen of the present invention are not particularly limited within the range in which the effects of the present invention are exhibited. Specific examples include amino acid derivatives, such as Dibutyl lauroyl glutamide; dextrin fatty acid esters, such as dextrin palmitic acid ester, dextrin stearic acid ester, and dextrin 2-ethylhexanoic acid palmitic acid ester; sucrose fatty acid esters, such as sucrose palmitic acid ester and sucrose stearic acid ester; benzylidene derivatives of sorbitol, such as monobenzylidene sorbitol and dibenzylidene sorbitol; organically modified clay minerals, such as dimethylbenzyldodecylammonium montmorillonite clay and dimethyldioctadecylammonium montmorillonite clay; and the like. These gelling agents can be contained singly or in combination of two or more in the emulsified cosmetic composition for use in sunscreen of the present invention.

The powders mentioned above as other components that can be contained in the emulsified cosmetic composition for use in sunscreen of the present invention are those that are used for general cosmetics (however, excluding the UV scattering agent as component (B)), and are not particularly limited within the range in which the effects of the present invention are exhibited. Specific examples include inorganic powders, organic powders, colored pigments, and the like. Further, their shape (e.g., spherical, needle-like, or plate-like), particle size (e.g., fumed, fine particles, or pigment-grade), and particle structure (e.g., porous or non-porous) is also not particularly limited.

The inorganic powders mentioned above are not particularly limited within the range in which the effects of the present invention are exhibited. Specific examples include magnesium oxide, barium sulfate, calcium sulfate, magnesium sulfate, calcium carbonate, magnesium carbonate, talc, synthetic mica, mica, kaolin, sericite, white mica, synthetic mica, gold mica, red mica, black mica, lithia mica, silicic acid, silicic anhydride, aluminum silicate, magnesium silicate, aluminum magnesium silicate, sulfur-containing aluminum silicate, calcium silicate, barium silicate, strontium silicate, metal tungstate, hydroxyapatite, vermiculite, Higilite®, montmorillonite, zeolite, ceramic powder, calcium monohydrogen phosphate, alumina, aluminum hydroxide, boron nitride, and the like.

The organic powders mentioned above are not particularly limited within the range in which the effects of the present invention are exhibited. Specific examples include polyamide powder, polyester powder, polyethylene powder, polypropylene powder, polystyrene powder, polyurethane, benzoguanamine powder, polymethylbenzoguanamine powder, tetrafluoroethylene powder, polymethylmethacrylate powder, silk powder, nylon powder, 12 nylon, 6 nylon, styrene-acrylic acid copolymers, divinylbenzene-styrene copolymers, vinyl resin, urea resin, phenol resin, fluororesin, silicon resin, acrylic resin, melamine resin, epoxy resin, polycarbonate resin, fine crystal fiber powder, lauroyl lysine, and the like.

The colored pigments mentioned above are not particularly limited within the range in which the effects of the present invention are exhibited. Specific examples include inorganic red pigments, such as iron oxide, iron hydroxide, and iron titanate; inorganic brown pigments, such as γ-iron oxide; inorganic yellow pigments, such as yellow iron oxide and ochre; inorganic black pigments, such as black iron oxide and carbon black; inorganic purple pigments, such as manganese violet and cobalt violet; inorganic green pigments, such as chromium hydroxide, chromium oxide, cobalt oxide, and cobalt titanate; inorganic blue pigments, such as prussian blue and ultramarine; pearl pigments, such as titanium oxide-coated mica, bismuth oxychloride, titanium oxide-coated bismuth oxychloride, titanium oxide-coated talc, fish scale foil, and titanium oxide-coated colored mica; metal powder pigments, such as aluminum powder, copper powder, and stainless steel powder; natural dyes, such as carminic acid, laccaic acid, carthamin, brazilin, crocin, and lakes thereof; pigments obtained by forming tar dyes into lakes, pigments obtained by forming natural dyes into lakes, composite powder that combines these powders, and the like.

The tar dyes mentioned above are not particularly limited within the range in which the effects of the present invention are exhibited. Specific examples include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207, and lakes thereof.

The powders mentioned above are not particularly limited within the range in which the effects of the present invention are exhibited. Specifically, powders surface-treated with an oily agent, silicone, or a fluorine compound, or composites of these can be used. Further, these components can be contained singly or in combination of two or more in the emulsified cosmetic composition for use in sunscreen of the present invention.

The form of the emulsified cosmetic composition for use in sunscreen of the present invention can be a wide range of general cosmetic forms, and is not particularly limited within the range in which the effects of the present invention are exhibited. Specific examples include lotion (liquid), mousse, gel, jelly, emulsion, suspension, cream, ointment, sheet, aerosol, spray, and the like.

The type of emulsion of the emulsified cosmetic composition for use in sunscreen of the present invention is not particularly limited within the range in which the effects of the present invention are exhibited. Examples include oil-in-water (O/W), water-in-oil (W/O), water-in-oil-in-water (W/O/W), oil-in-water-in-oil (O/W/O), and the like. When the continuous phase of the sunscreen emulsified cosmetic composition is an aqueous phase, the emulsified cosmetic composition can have a fresh and refreshing texture. When the continuous phase is an oil phase, the emulsified cosmetic composition can have high water resistance and excellent sustainability.

The type of the cosmetic composition for use in sunscreen of the present invention is not particularly limited within the range in which it is applied to the skin or hair and the effects of the present invention are exhibited. Specific examples include base make-up cosmetics, such as foundation and makeup base; basic skin care cosmetics, such as lotion, emulsion, and cream; hair sunscreen cosmetics; and the like.

Since the emulsified cosmetic composition for use in sunscreen of the present invention contains trans-resveratrol polysaccharide, it can be expected to exhibit the various actions exhibited by conventionally known trans-resveratrol or polysaccharides thereof, such as antioxidant action on the skin (including the scalp) or hair (action to inhibit the Maillard reaction in vivo, action to enhance the expression of sirtuin genes, action to suppress the expression of NFκB, which is a transcription factor that induces inflammation, and action to suppress the growth of *Propionibacterium acnes*).

The emulsified cosmetic composition for use in sunscreen of the present invention can be produced by a known method, regardless of the type of emulsion of the sunscreen cosmetic of the present invention, and the method is not particularly limited. For example, resveratrol polysaccharide as component (A) is dissolved in an aqueous phase, UV protection agent (B) is dissolved or dispersed in an oil phase, and both phases are mixed by a predetermined method. When using such a production method, resveratrol polysaccharide as component (A) is present in the aqueous phase, and UV protection agent (B) is present in the oil phase, whereby an emulsified cosmetic composition for use in sunscreen with superior texture, usability, or sustainability can be obtained.

EXAMPLES

Examples are provided below to describe the sunscreen emulsified cosmetic composition of the present invention in detail. Needless to say, the present invention is not limited to the following Examples. In the following description, the amounts in the formulations are mass % with respect to the total amount, unless otherwise specified.

The trans-resveratrol polysaccharide contained in the sunscreen emulsified cosmetic composition of the present invention used in the Examples is a mixture of compounds represented by the following formula (1), wherein n is 0, 1, 2, 3, 4, 5, 6, 7, 8, and 9 (produced by Meisterbio Co., Ltd.):

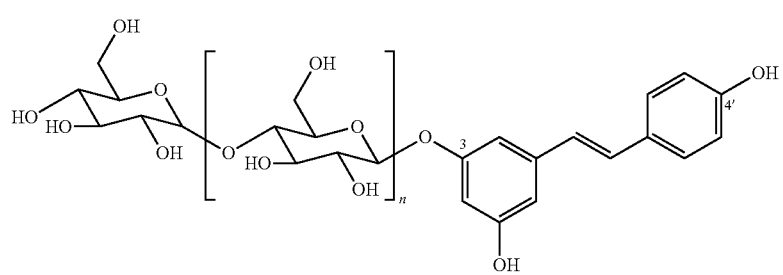

(1)

wherein all (1-4) glycosidic linkages in the formula are α-linkages, and
an O-glycosidic linkage at position 3 of resveratrol in the formula is a β-linkage.

The trans-resveratrol polysaccharide used in the Examples was a compound having 3 to 5 sugars on average. The amount of the compound wherein n is 0 (trans-resveratrol monosaccharide glycoside) was 25.8 mass % based on 100 mass % of the mixture.

The method for evaluating the cosmetic compositions for use in sunscreen of the following Examples and Comparative Examples are as described below.
Sunscreen Effect The sunscreen effect was measured as an SPF value (in vitro) using an SPF Analyzer UV-1000S (produced by Labshere). The sample application plate used was SPFMAS-TER-PA01 (produced by Shiseido Irica Technology Inc.). 2 mg/cm$^2$ of each sample was applied thereto for measurement. To confirm the synergistic effect of the emulsified cosmetic composition for use in sunscreen of the present invention from the SPF values, it can be confirmed by comparing the sum of the SPF value of a sample containing an active ingredient (e.g. a UV protection agent) alone, and the SPF value of a sample containing another active ingredient (e.g. trans-resveratrol polysaccharide) alone, with the SPF value of a sample containing both active ingredients. The synergistic effect can also be evaluated, for example, by a numerical value obtained by dividing the SPF value of the sample containing both active ingredients by the sum of the SPF values of the samples containing each active ingredient alone.
Sensory Evaluation For the following 3 items (a, b, and c), 10 experienced panelists used each sample and scored it on a scale of 1 to 5 according to "(1) Evaluation criteria" below. From the total score of the 10 panelists, the effects of the sunscreen emulsified cosmetic compositions obtained in the Examples and Comparative Examples were determined according to "(2) 4-Grade criteria" below. The experienced panelists are persons who are good at evaluating these items and who can reflect the adjustment of the scores between the panelists when determining the following evaluation criteria.
Items
 a. No stickiness (texture)
 b. Ease of spreading (usability)
 c. No white cast
(1) Evaluation Criteria
(Score): (Evaluation)
 5: Good
 4: Slightly good
 3: Normal
 2: Slightly bad
 1: Bad
(2) 4-Grade Criteria
(Determination): (Total Score)
 ⊚: The total score was 41 to 50 points.
 ○: The total score was 31 to 40 points.
 Δ: The total score was 21 to 30 points.
 X: The total score was 5 to 20 points.
Oil-In-Water (O/W) Cosmetic Composition According to the following production procedure, O/W cosmetic compositions of the formulations shown in Tables 1 and 2 below were prepared, and evaluated in the above manner. The results are also shown in Tables 1 and 2.
Production Procedure
(1) The components of A phase (surfactant phase) were mixed.
(2) The components of B phase (oil phase) were mixed.

(3) A small amount of the mixture of the components of B phase was gradually added to the mixture of the components of A phase at room temperature, thereby preparing a gel emulsion.
(4) The gel emulsion was mixed with the components of C phase (aqueous phase), thereby preparing an O/W cosmetic composition.

TABLE 1

| Phase | | | Example 1 | Comparative Example 1 | Comparative Example 2 | Comparative Example 3 | Comparative Example 4 | Comparative Example 5 | Comparative Example 6 |
|---|---|---|---|---|---|---|---|---|---|
| A | 1 | Glycerin | 8.00 | 8.00 | 8.00 | 8.00 | 8.00 | 8.00 | 8.00 |
|   | 2 | Isostearic add | 3.00 | 3.00 | 3.00 | 3.00 | 3.00 | 3.00 | 3.00 |
|   | 3 | Potassium hydroxide | 0.60 | 0.60 | 0.60 | 0.60 | 0.60 | 0.60 | 0.60 |
|   | 4 | Purified water | 0.50 | 0.50 | 0.50 | 0.50 | 0.50 | 0.50 | 0.50 |
| B | 5 | Triethylhexanoin | 13.00 | 13.00 | 13.00 | 13.00 | 13.00 | 13.00 | 13.00 |
|   | 6 | Sorbitan oleate | 0.30 | 0.30 | 0.30 | 0.30 | 0.30 | 0.30 | 0.30 |
|   | 7 | Hydrophobized fine particle titanium oxide (*1) | 8.00 | — | 8.00 | 8.00 | 8.00 | 13.00 | — |
|   | 8 | Hydrophobized titanium oxide (*2) | — | — | — | — | — | — | 8.00 |
|   | 9 | Trans-resveratrol (*3) | — | — | — | 5.00 | — | — | — |
| C | 10 | Trans-resveratrol polysaccharide | 5.00 | 5.00 | — | — | — | — | 5.00 |
|   | 11 | Trans-resveratrol monosaccharide glycoside (*4) | — | — | — | — | 5.00 | — | — |
|   | 12 | Propanediol | 8.00 | 0.30 | 0.30 | 0.30 | 0.30 | 0.30 | 8.00 |
|   | 13 | Carbomer | 0.30 | 0.30 | 0.30 | 0.30 | 0.30 | 0.30 | 0.30 |
|   | 14 | Phenoxyethanol | 0.50 | 0.50 | 0.50 | 0.50 | 0.50 | 0.50 | 0.50 |
|   | 15 | Purified water | Remnant | Remnant | Remnant | Remnant | Remnant | Remnant | Remnant |
|   |   | Total | 100.00 | 100.00 | 100.00 | 100.00 | 100.00 | 100.00 | 100.00 |
| Evaluation |   | SPF value | 37.6 | 9.6 | 10.1 | 11.9 | *5 | 47.9 | 27.3 |
|   |   | No stickiness | ◎ | ◎ | ◎ | Δ | | ○ | ◎ |
|   |   | No white cast | ○ | ◎ | ○ | ○ | | Δ | X |
|   |   | Ease of spreading | ○ | ○ | ○ | ○ | | X | ○ |

(*1) Triethoxycaprylylsilane-treated fine particle titanium oxide having a number average particle size of 10 nm (MTX-05OTS, produced by Tayca Corporation)
(*2) Triethoxycaprylylsilane-treated titanium oxide having a number average particle size of 250 nm (OTS-2 TiO2 CR50, produced by Tayca Corporation)
(*3) Resveratrol aglycone (ATTO)
(*4) Piceid (resveratrol monosaccharide glycoside, ATTO)
(*5) Component 11 (resveratrol monosaccharide glycoside) could not be dissolved uniformly in the aqueous phase, and a desired cosmetic composition could not be prepared.

As is clear from the results shown in Table 1, the O/W cosmetic composition of Example 1 containing "7. Hydrophobized fine particle titanium oxide," which was a UV protection agent, and "10. Trans-resveratrol polysaccharide" showed an SPF value as high as 37.6 without impairing the excellent texture and usability. Since the SPF value of Comparative Example 1 containing "10. Trans-resveratrol polysaccharide" alone as an active ingredient was 9.6, and the SPF value of Comparative Example 2 containing "7. Hydrophobized fine particle titanium oxide" alone as an active ingredient was 10.1, the SPF value of Example 1 simultaneously containing both of them was 1.9 times the sum of the SPF values of the respective active ingredients. Therefore, it could be determined that the cosmetic composition containing both trans-resveratrol polysaccharide and hydrophobized fine particle titanium oxide exhibited a synergistic effect.

Compared with the SPF value of Comparative Example 1 containing "7. Hydrophobized fine particle titanium oxide" alone, the sunscreen cosmetic of Comparative Example 3 simultaneously containing "9. Trans-resveratrol aglycone," which was not a polysaccharide, and "7. Hydrophobized fine particle titanium oxide" did not show a significant improvement as indicated by the SPF value of Example 1 containing "10. Trans-resveratrol polysaccharide." As shown in Comparative Example 4, piceid, which was "11. Trans-resveratrol monosaccharide glycoside," could not be dissolved in C phase (aqueous phase), and an emulsified cosmetic composition for use in sunscreen of a desired formulation could not be produced. Since it is generally difficult to apply the formulation that could not be produced in such a small lot experiment to mass production, the production of emulsified cosmetic compositions for use in sunscreen containing trans-resveratrol monosaccharide glycoside turned out to be impractical.

Comparative Example 5 containing a significant amount of "7. Hydrophobized fine particle titanium oxide," which was a conventionally used UV scattering agent, showed an excellent SPF value, but was inferior to Example 1 in all of the evaluation items, i.e., non-stickiness, no white cast, and ease of spreading. It could not be readily determined that the emulsified cosmetic composition for use in sunscreen of this formulation was superior.

When using "8. Hydrophobized titanium oxide," which had a number average particle size of 250 nm and was conventionally used for white pigments in cosmetic compositions, as the titanium oxide to be combined with "10. Trans-resveratrol polysaccharide," as shown in Comparative Example 6, the SPF value was 27.3, which was inferior to the SPF value (37.6) of Example 1. In addition, white cast turned out to be significant. These results clarified that the titanium oxide that exhibited a synergistic effect when mixed together with "10. Trans-resveratrol polysaccharide" in the emulsified cosmetic composition for use in sunscreen was "7. Hydrophobized fine particle titanium oxide," which exhibited a UV protection effect, rather than titanium oxide generally used for white pigments.

TABLE 2

| Phase | | | Example 2 | (Comparative Example 1) | Comparative Example 7 | Comparative Example 8 |
|---|---|---|---|---|---|---|
| A | 1 | Glycerin | 8.00 | 8.00 | 8.00 | 8.00 |
| | 2 | Isostearic acid | 3.00 | 3.00 | 3.00 | 3.00 |
| | 3 | Potassium hydroxide | 0.60 | 0.60 | 0.60 | 0.60 |
| | 4 | Purified water | 0.50 | 0.50 | 0.50 | 0.50 |
| B | 5 | Triethylhexanoin | 13.00 | 13.00 | 13.00 | 13.00 |
| | 6 | Sorbitan oleate | 0.30 | 0.30 | 0.30 | 0.30 |
| | 7 | Ethylhexyl methoxycinnamate | 5.00 | — | 5.00 | 10.00 |
| C | 8 | Trans-resveratrol polysaccharide | 5.00 | 5.00 | — | — |
| | 9 | Propanediol | 8.00 | 0.30 | 0.30 | 0.30 |
| | 10 | Carbomer | 0.30 | 0.30 | 0.30 | 0.30 |
| | 11 | Phenoxyethanol | 0.50 | 0.50 | 0.50 | 0.50 |
| | 12 | Purified water | Adequate amount | Adequate amount | Adequate amount | Adequate amount |
| Evaluation | | SPF value | 21.5 | 9.6 | 10.1 | 14.8 |
| | | No stickiness | ○ | ◎ | ○ | Δ |
| | | No white cast | ◎ | ◎ | ◎ | ◎ |
| | | Ease of spreading | ◎ | ◎ | ◎ | Δ |

From the results shown in Table 2, the emulsified cosmetic composition of the formulation of Example 2, which used "8. Trans-resveratrol polysaccharide" and "7. Ethylhexyl methoxycinnamate," as a UV absorbing agent, which was a UV protection agent, showed an SPF value as high as 21.5. The SPF value of Comparative Example 1 containing "8. Trans-resveratrol polysaccharide" alone as an active ingredient was 9.6, and the SPF value of Comparative Example 7 containing "7. Ethylhexyl methoxysilicate" alone as an active ingredient was 10.1. Therefore, the SPF value of Example 2 exceeds the sum of these SPF values, and it could thus be determined that a synergistic effect including trans-resveratrol and the UV absorbing agent was exhibited. In addition, as shown in Comparative Example 8, when the amount of "7. Ethylhexyl methoxysilicate" was increased twice, the SPF value increased to 14.8; however, this increase was merely a little less than 1.5 times, and it was clarified that the evaluations of no stickiness and ease of spreading were reduced.

Water-In-Oil (W/O) Sunscreen Cosmetic

According to the following production procedure, W/O cosmetic compositions of the formulations shown in Tables 3 and 4 below were prepared, and evaluated in the above manner. The results are also shown in Tables 3 and 4.

Production Procedure
(1) The components of A phase were mixed.
(2) The components of B phase were mixed.
(3) A small amount of the mixture of the components of B phase was gradually added, while stirring, to the mixture of the components of A phase at room temperature, thereby preparing a water-in-oil cosmetic.

TABLE 3

| Phase | | | Example 3 | Example 4 | Example 5 | Example 6 | Comparative Example 9 | Comparative Example 10 | Comparative Example 11 |
|---|---|---|---|---|---|---|---|---|---|
| A | 1 | Polyglyceryl-2 monoisostearate | 0.20 | 0.20 | 0.20 | 0.20 | 0.20 | 0.20 | 0.20 |
| | 2 | Polyglyceryl-2 disostearate | 3.00 | 3.00 | 3.00 | 3.00 | 3.00 | 3.00 | 3.00 |
| | 3 | Cyclopentasiloxane | 21.00 | 21.00 | 21.00 | 21.00 | 21.00 | 21.00 | 21.00 |
| | 4 | Neopentyl glycol dicaprate | 3.00 | 3.00 | 3.00 | 3.00 | 3.00 | 3.00 | 3.00 |
| | 5 | Disteardimonium hectorite | 0.40 | 0.40 | 0.40 | 0.40 | 0.40 | 0.40 | 0.40 |
| | 6 | PEG-10 dimethicone | 7.00 | 7.00 | 7.00 | 7.00 | 7.00 | 7.00 | 7.00 |
| | 7 | Hydrophobized fine particle titanium oxide 10 nm (*6) | 8.40 | | | | | | 8.40 |
| | 8 | Hydrophobized fine particle titanium oxide 15 nm (*7) | | 8.40 | | | | | |
| | 9 | Hydrophobized fine particle titanium oxide 35 nm (*8) | | | 8.40 | | | | |

TABLE 3-continued

| Phase | | | Example 3 | Example 4 | Example 5 | Example 6 | Comparative Example 9 | Comparative Example 10 | Comparative Example 11 |
|---|---|---|---|---|---|---|---|---|---|
| | 10 | Hydrophobized fine particle titanium oxide 80 nm (*9) | | | | 8.40 | | | |
| | 11 | Hydrophobized titanium oxide 250 nm (*2) | | | | | 8.40 | | |
| B | 12 | Trans-resveratrol polysaccharide | 5.00 | 5.00 | 5.00 | 5.00 | 5.00 | 5.00 | |
| | 13 | Butylene glycol | 8.00 | 8.00 | 8.00 | 8.00 | 8.00 | 8.00 | 8.00 |
| | 14 | Methylparaben | 0.10 | 0.10 | 0.10 | 0.10 | 0.10 | 0.10 | 0.10 |
| | 15 | Purified water | Remnant | Remnant | Remnant | Remnant | Remnant | Remnant | Remnant |
| | | Total | 100.00 | 100.00 | 100.00 | 100.00 | 100.00 | 100.00 | 100.00 |
| Evaluation | | SPF value | 32.1 | 32.2 | 34.6 | 17.6 | 16.2 | 4.1 | 15.6 |
| | | No stickiness | ○ | ○ | ○ | ○ | ○ | ◎ | ○ |
| | | No white cast | ○ | ○ | ○ | Δ | X | ◎ | ○ |
| | | Ease of spreading | ○ | ○ | ○ | ○ | ○ | ◎ | ○ |

(*2) Triethoxycaprylylsilane-treated titanium oxide having a number average particle size of 250 nm (OTS-2 TiO2 CR50, produced by Tayca Corporation)
(*6) Aluminum stearate-treated titanium oxide having a number average particle size of 10 nm (MT-01, produced by Tayca Corporation)
(*7) Hydrogen dimethicone-treated titanium oxide having a number average particle size of 15 nm (MTY-100SAS, produced by Tayca Corporation)
(*8) Hydrogen dimethicone-treated titanium oxide having a number average particle size of 35 nm (MTY-500SAS, produced by Tayca Corporation)
(*9) Hydrogen dimethicone-treated titanium oxide having a number average particle size of 80 nm (MTY-700BS, produced by Tayca Corporation)

As is clear from the results shown in Table 3, the O/W sunscreen cosmetic of Example 3 containing "7. Hydrophobized fine particle titanium oxide 10 nm" as a UV protection agent and "12. Trans-resveratrol polysaccharide" showed an SPF value as high as 32.1 without impairing the excellent texture and usability. Since the SPF value of Comparative Example 11 containing "7. Hydrophobized fine particle titanium oxide 10 nm" alone as an active ingredient was 15.6, and the SPF value of Comparative Example 10 containing "10. Trans-resveratrol polysaccharide" alone as an active ingredient was 4.1, the SPF value of Example 3 containing both of them turned out to be 1.9 times the sum of the SPF values of the respective active ingredients. Therefore, it could be determined that, regardless of whether it was a W/O cosmetic composition or an O/W cosmetic composition, the cosmetic composition containing both hydrophobized fine particle titanium oxide and trans-resveratrol glycoside synergistically increased the SPF effect exerted by each component.

Similar to the results of the O/W cosmetic compositions shown in Table 1 above, the results of Comparative Example 9 revealed that when titanium oxide having a primary particle size of about 250 nm, which is generally used as a white pigment in cosmetic compositions, as with "11. Hydrophobized titanium oxide," was used together with "12. Trans-resveratrol polysaccharide," a high SPF value was not shown, unlike fine particle titanium oxide having an excellent UV protection effect. In addition, the evaluation of white cast was significantly inferior to the results shown in Examples 3 to 6. The results of Examples 3 to 6 also clarified that the particle size of titanium oxide that exhibited a synergistic effect and showed a high sunscreen effect without white cast was around 10 nm to 100 nm.

TABLE 4

| Phase | | | Example 7 | (Comparative Example 10) | Comparative Example 12 |
|---|---|---|---|---|---|
| A | 1 | Polyglyceryl-2 monoisostearate | 0.20 | 0.20 | 0.20 |
| | 2 | Polyglyceryl-2 diisostearate | 3.00 | 3.00 | 3.00 |
| | 3 | Cyclopentasiloxane | 21.00 | 21.00 | 21.00 |
| | 4 | Neopentyl glycol dicaprate | 3.00 | 3.00 | 3.00 |
| | 5 | Disteardimonium hectorite | 0.40 | 0.40 | 0.40 |
| | 6 | PEG-10 dimethicone | 7.00 | 7.00 | 7.00 |
| | 7 | Hydrophobized fine particle zinc oxide 35 nm (*10) | 13.00 | | 13.00 |
| B | 8 | Trans-resveratrol polysaccharide | 5.00 | 5.00 | |
| | 9 | Butylene glycol | 8.00 | 8.00 | 8.00 |
| | 10 | Methylparaben | 0.10 | 0.10 | 0.10 |
| | 11 | Purified water | Remnant | Remnant | Remnant |
| | | Total | 100.00 | 100.00 | 100.00 |
| Evaluation | | SPF value | 19.5 | 4.1 | 8.8 |
| | | No stickiness | ○ | ◎ | ○ |
| | | No white cast | ○ | ◎ | ○ |
| | | Ease of spreading | ○ | ◎ | ○ |

(*10) Hydrogen dimethicone-treated zinc oxide having a number average particle size of 35 nm (MZ-303S, produced by Tayca Corporation)

From the results shown in Table 4, the emulsified cosmetic composition of the formulation of Example 7, which used "8. Trans-resveratrol polysaccharide" and "7. Hydrophobized fine particle zinc oxide 35 nm" as a UV scattering agent, which was a UV protection agent, showed an SPF value as high as 19.5. Since the SPF value of Comparative Example 10 containing "8. Trans-resveratrol polysaccharide" alone as an active ingredient was 4.1, and the SPF value of Comparative Example 12 containing "7. Hydrophobized fine particle zinc oxide 35 nm" alone as an active ingredient was 8.8, the SPF value of Example 7 containing both of them was 1.5 times the sum of the SPF values of the respective active ingredients. Therefore, it could be determined that a synergistic effect could be obtained even when using fine particle zinc oxide as a UV scattering agent.

The invention claimed is:

1. An emulsified cosmetic composition for use in sunscreen, comprising the following components (A) and (B):
(A) trans-resveratrol polysaccharide, wherein the trans-resveratrol polysaccharide comprises a compound represented by formula (1):

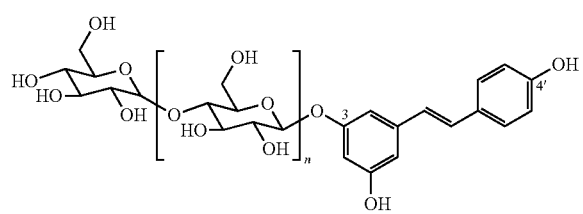

(1)

wherein n is an integer of 1 to 9,
wherein all (1-4) glycosidic linkages in the formula are α-linkages, and
wherein an O-glycosidic linkage at position 3 of resveratrol in the formula is a β-linkage; and
(B) a UV protection agent, wherein the UV protection agent is a UV scattering agent, wherein the UV scattering agent is selected from the group consisting of fine particle titanium oxide, fine particle zinc oxide, and combinations thereof; wherein the UV scattering agent has a hydrophobized surface and wherein the UV scattering agent has a number average particle size of from 10 nm to 35mn.

2. The emulsified cosmetic composition according to claim 1, wherein the trans-resveratrol polysaccharide is a compound in which a plurality of sugars are O-glycosidically linked to a hydroxyl group of trans-resveratrol.

3. The emulsified cosmetic composition according to claim 1, wherein the trans-resveratrol polysaccharide further comprises compounds represented by formula (2), formula (3), or a combination thereof:

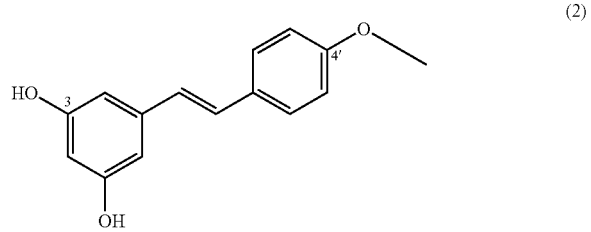

(2)

-continued

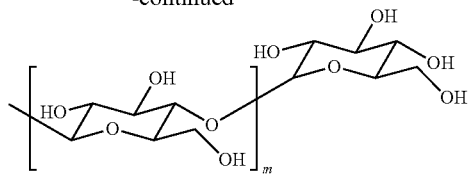

wherein m is an integer of 1 to 9,
all (1-4) glycosidic linkages in the formula are α-linkages, and
an O-glycosidic linkage at position 4' of resveratrol in the formula is a β-linkage;

(3)

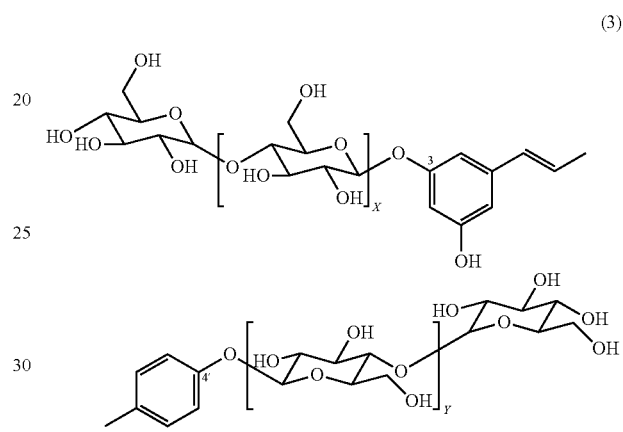

wherein X and Y are an integer of 0 to 9, and the sum of X and Y is 15 or less,
all (1-4) glycosidic linkages in the formula are α-linkages, and
O-glycosidic linkages at positions 3 and 4' of resveratrol in the formula are β-linkages.

4. The emulsified cosmetic composition according to claim 1, further comprising a UV absorbing agent.

5. The emulsified cosmetic composition according to claim 1, wherein the UV scattering agent comprises the fine particle titanium dioxide.

6. The emulsified cosmetic composition according to claim 1, wherein the UV scattering agent consists of the fine particle titanium dioxide.

7. The emulsified cosmetic composition according to claim 1, wherein the UV scattering agent consists of the fine particle zinc oxide.

8. The emulsified cosmetic composition according to claim 1, wherein the trans-resveratrol polysaccharide is present in an amount of from about 0.0001% to about 30%, based on the total weight of the emulsified cosmetic composition.

9. The emulsified cosmetic composition according to claim 1, wherein the trans-resveratrol polysaccharide is present in an amount of from about 0.1% to about 25%, based on the total weight of the emulsified cosmetic composition.

10. The emulsified cosmetic composition according to claim 1, wherein the trans-resveratrol polysaccharide is present in an amount of from about 1% to about 20%, based on the total weight of the emulsified cosmetic composition.

* * * * *